(12) United States Patent
Lin et al.

(10) Patent No.: US 8,525,980 B2
(45) Date of Patent: Sep. 3, 2013

(54) BODY FLUID DETECTION METHOD USING SURFACE ENHANCED RAMAN SPECTROSCOPY

(76) Inventors: Juqiang Lin, Fujian (CN); Rong Chen, Fujian (CN); Shangyuan Feng, Fujian (CN); Yongzeng Li, Fujian (CN); Guannan Chen, Fujian (CN); Zufang Huang, Fujian (CN); Min Cheng, Fujian (CN); Yun Yu, Fujian (CN); Haishan Zeng, Fujian (CN)

(*) Notice: Subject to any disclaimer, the term of this patent is extended or adjusted under 35 U.S.C. 154(b) by 173 days.

(21) Appl. No.: 13/255,911

(22) PCT Filed: Jun. 21, 2010

(86) PCT No.: PCT/CN2010/074126
§ 371 (c)(1),
(2), (4) Date: Sep. 11, 2011

(87) PCT Pub. No.: WO2011/130937
PCT Pub. Date: Oct. 27, 2011

(65) Prior Publication Data
US 2012/0062885 A1    Mar. 15, 2012

(30) Foreign Application Priority Data
Apr. 19, 2010    (CN) .......................... 2010 1 0149269

(51) Int. Cl.
*G01N 1/00* (2006.01)
*G01N 21/00* (2006.01)

(52) U.S. Cl.
CPC . *G01N 1/00* (2013.01); *G01N 21/00* (2013.01)
USPC .............................................. 356/36; 356/344

(58) Field of Classification Search
CPC .......... G01N 33/48; G01N 1/00; G01N 21/00
USPC .............................................. 356/36–42, 344
See application file for complete search history.

(56) References Cited

U.S. PATENT DOCUMENTS

| | | | |
|---|---|---|---|
| 2001/0053521 A1* | 12/2001 | Kreimer et al. | 435/6 |
| 2008/0074661 A1* | 3/2008 | Zhang et al. | 356/301 |
| 2009/0219526 A1* | 9/2009 | Davisson et al. | 356/301 |
| 2011/0162441 A1* | 7/2011 | Martin et al. | 73/64.56 |

* cited by examiner

Primary Examiner — Michael P Stafira

(57) ABSTRACT

This invention provides a body fluid detection method by using surface enhanced Raman spectroscopy. In this method, some biological macromolecules in body fluid samples could be separated with membrane electrophoresis technique firstly. Next, samples are cut off along with the substrates and touched with glacial acetic acid. Transparent colloid formed while incubating. Then add enhancing substrates and continue to incubate and stir. When solid impurities precipitated, stop incubating and stand for layering. In the end, take upper layer resulted to be tested using SERS detection method and build SERS database. This invention successfully eliminated disturbance of other complex components on the SERS detection of protein, DNA and RNA. High quality SERS spectrum obtained is beneficial to the analysis and process of SERS spectrum. Thus body fluid can be differentiated by comparing body fluid SERS spectrum belonging to the healthy people and patients.

8 Claims, 5 Drawing Sheets

BODY FLUID DETECTION METHOD USING SURFACE ENHANCED RAMAN SPECTROSCOPY

FIELD OF THE INVENTION

The invention is concerned with detection method, especially relevant to the method of body fluid detection using surface enhanced Raman spectroscopy.

BACKGROUND OF THE INVENTION

Raman spectroscopy is a spectroscopic technique which can provide vibration spectrum of molecules. Based upon this, it can detect and get the information of structure and composition of samples at the molecular level because of changes in histiocyte inevitably lead to structural and compositional variation in both intracellular and extracellular biomolecules. Due to its weakness, however, normal Raman signal for detection needs to be enhanced by means of certain techniques, one of which is surface enhanced Raman spectroscopy (SERS). SERS is a technique that enhances Raman scattering by $10^4$-$10^6$ times through molecules adsorbed on rough metal (e.g. Au, Ag, Cu and Pt) surfaces. In theory. SERS is highly surface-sensitive enough to detect single molecule. On the other hand, use of near infrared ray excitation (785 nm) in SERS result in detection power lower than 1 mW, realizing nondestructive testing of biological samples.

Membrane electrophoresis is an electrophoretic technique especially suitable for the separation and analysis of body fluid like blood. So far it has wide application in the segregation analysis of serum protein, hemoglobin, globulin, lipoprotein, glucoprotein, alpha fetoprotein, steroids and isozyme. Compared with other electrophoretic techniques such as polyacrylamide gel electrophoresis and agarose gel electrophoresis, membrane electrophoresis has the following advantages:

(1) Fast and time-saving. Take cellulose acetate membrane electrophoresis for instance, less chamber buffer cellulose acetate membrane contains reduces electrodialysis, current thus is mainly conducted by samples, making it fast to separate. Also shorter time will be used for electrophoresis (40-60 min).

(2) High sensitivity and sample-saving. Take blood for instance, only 0.1-2 μl serum is enough for a clear separation band.

(3) High specificity. Take cellulose acetate electrophoresis for instance, there is no tailing because few impurities are adsorbed by cellulose acetate film. Specificity thus can be increased by clear separation band obtained through complete fading of background after staining.

The principle of membrane electrophoresis is explained as follows:
(1) Take separation and analysis of serum protein for example. As is known, the isoelectric point of most serum protein is less than pH of 7.0. In barbital buffer solution with pH of 8.6, serum protein electrified by the anions it ionizes can move to the oppositely charged electrodes under the influence of the electric field, which is known as electrophoresis.
(2) In general, membrane electrophoresis is named after the film substrate used. For instance, cellulose acetate electrophoresis is named after the cellulose acetate film substrate. In a condition with the same pH value, charges on different kinds of serum proteins vary resulting from different composition, molecular weight, isoelectric point and shape of the serum protein amino acid. Proteins with less molecular weight carry more charges, and move faster. Whereas proteins with greater molecular weight carry less charges, and move slower. In this way, serum protein can be separated via difference of speeds.

Pathological changes histiocytes undergo often display in three kinds of biomolecules, that is protein, DNA and RNA. But components of body fluid and secretion is complicated. Take blood for example, it comprises of not only serum protein, but also glucose, fat, hormone and xenobiotics such as pharmaceuticals, bacteria and virus. It is difficult to further analyze protein, DNA and RNA using SERS spectrum with traditional approaches which focus on direct SERS detection because SERS spectrum is so sensitive that Raman signals of every part of samples is enhanced, disturbing SERS signals emitted by protein, DNA and RNA in the body fluid.

SUMMARY OF THE INVENTION

This invention is aimed at providing a method of body fluid detection using surface enhanced Raman spectroscopy which can eliminate disturbance from other complex components in body fluid on the protein, DNA and RNA molecules.

Specific steps: a) treat liquid sample into aqueous phase (upper) and solid phase (bottom); b) divide the upper aqueous phase equally into two parts and electrophorese proper amount of each part simultaneously; c) after that, stain one of the parts to compare with the position of the other unstained part located in the membrane electrophoresis substrates; d) cut off unstained samples together with substrates at the same position; e) contact the unstained part with proper solvent and incubate the samples at a certain temperature to generate limpid colloid. Then add enhancing substrates for Raman spectrum. Mix them up and keep incubating. Stop incubating when solid impurities precipitate. Take mixture of body fluid and enhancing substrates which is the upper layer formed while standing to be tested through surface enhanced spectroscopy; f) set SERS spectrum database by repetition with different samples following the same procedures as described above; g) carry out cluster analysis of SERS database using suitable method to build a SERS analytical model.

In accordance with steps descried above, SERS of normal persons and patients can be obtained. Principal component analysis (PCA) is applied in building a SERS analytical model. Based on it, distribution of scattering points corresponding to the body fluid samples of normal persons and patients is generated. Thus body fluids can be differentiated by comparing body fluids SERS spectrum belonging to two kinds of persons.

The advantage of this invention is elimination of disturbance of other components on proteins, DNA and RNA molecules in SERS detection, bringing high sensitivity of SERS into full play. This helps to access to high quality body fluid surface enhanced Raman spectroscopy with which SERS spectrum can be analysed better for valuable information.

Technical setup to reach the aim of this invention:

1. Preparation of SERS Enhancing Substrates silver sol or gold sol with diameter of 40-70 nm is prepared by reducing Ag or Au with hydroxylamine hydrochloride, sodium citrate or sodium borate.

Three kinds of methods involving preparation of silver sol or gold sol are described as follows.

(1) Hydroxylamine hydrochloride is dissolved in water, followed by the addition of sodium hydroxide solution. The hydroxylamine/sodium hydroxide solution was then added rapidly to the silver nitrate solution under vigorous stirring. Then a grey-brown silver sol resulted, which is rotated in centrifuge at 4000-5000 rpm for 10-15 min. Then discard the upper clear layer of separated mixture and seal the bottom condensed layer of silver sol in the dark at room temperature for use. The molar ratio of sodium hydroxide:hydroxylamine hydrochloride:silver nitrate in the above preparation process is 1:0.6:0.011.

(2) 10 mg of silver nitrate is dissolved in 50 ml of deionized water and brought to boiling at 100° C. A solution of 2% sodium citrate (1 ml) is added portionwise with vigorous stirring. The solution is kept on boiling for six hours. Let the silver sol resulted cool naturally, followed by separation with centrifuge. Discard the upper clear layer and seal the bottom layer of condensed silver sol in the dark at room temperature for use.

(3) 10 mg of chloroauric acid is dissolved in 100 ml of deionized water and brought to boiling at 100° C. A solution of 1% sodium citrate (2 ml) is dropped with vigorous stirring. The solution is kept on boiling for fifteen minutes. Let the gold sol resulted cool naturally, followed by separation with centrifuge. Discard the upper clear layer and seal the bottom layer of condensed gold sol in the dark at room temperature for use.

2. Membrane Electrophoresis a) Treat the liquid sample into aqueous phase (upper) and solid phase (bottom)
b) Divide the upper aqueous phase equally into two parts and electrophorese proper amount of each part simultaneously
c) When membrane electrophoresis is finished, blot one of the two parts using protein staining or nucleic acid (DNA or RNA) staining method for comparison with position of the other unstained part located in the membrane electrophoresis substrates.
d) Cut off the unstained samples together with substrates at the same position.

3. Preparation of mixed solution of the unstained body fluid and SERS enhancing substrates Under an appropriate condition, bring unstained samples to contacting with 150 µl-500 µl of solvent, such as glacial acetic acid, trimethylol aminomethane-hydrochloric acid buffer or trimethylol aminomethane-hydrochloric acid buffer without ribonuclease. Then the mixture is incubated at 25-65° C. for 10-40 minutes. The transparent colloid thus formed is added with SERS enhancing substrates and kept on incubating and stirring. Stop incubation when solid impurities precipitate. Select the mixed solution of unstained body fluid sample and SERS enhancing substrates which is the upper layer formed while standing for SERS detection and discard the bottom solid impurities layer.

4. Detection of Mixed Solution of Body Fluid and SERS Enhancing Substrates

Irradiate the mixed solution mentioned above with laser light ($\lambda$=400-850 nm) to detect Raman signal using Raman spectroscopy with selected spectral range of 400-4000 cm$^{-1}$.

5. Building SERS Analytical Model

Build database based upon SERS data derived from the above four steps involving body fluid of different persons. Carry out cluster analysis of SERS database using Principal component analysis (PCA) and then build a SERS analytical model in order to obtain a scatterplot corresponding to different body fluid samples.

6. Identification of SERS of Normal People and Patients.

Based on the five steps above, respective SERS of normal people and patients' body fluid is obtained in order to build SERS database: the PCA method is applied in the cluster analysis of the database to build SERS analytical model, then the scatterplot is made. Thus body fluid can be differentiated by comparing body fluid SERS belonging to two kinds of persons, which is applicable in the diagnosis and screening of diseases.

SERS enhancing substrates mentioned in the above steps is silver sol or gold sol; Body fluid mentioned above includes blood, serum, lymph, cerebrospinal fluid, urine, saliva, lacrimal fluid, sweat, cell extracts, tissue homogenate, vaginal discharge or seminal fluid; Unstained body fluid samples mentioned above are protein, DNA or RNA molecules segregated from body fluid samples;

Protein staining method described above is amido black staining or coomassie brilliant blue staining method; while nucleic acid staining method refers to ethidium bromide staining or silver staining method;

Mixed solution mentioned above is protein-silver sol, protein-gold sol, DNA-silver sol, DNA-gold sol, RNA-silver sol. RNA-gold sol mixed solution;

Process mentioned above involving preparation of mixed body fluid-enhancing SERS substrates solution comprises of three steps, that is, solvent treating, incubating and layering. Substrates used in membrane electrophoresis described above is cellulose acetate membrane, nitrocellulose membrane, nylon membrane or polyvinylidene fluoride membrane.

FIG. 1 shows preparation and SERS detection of the mixed body fluid-SERS enhancing substrates solution in this invention.

Figure 1:
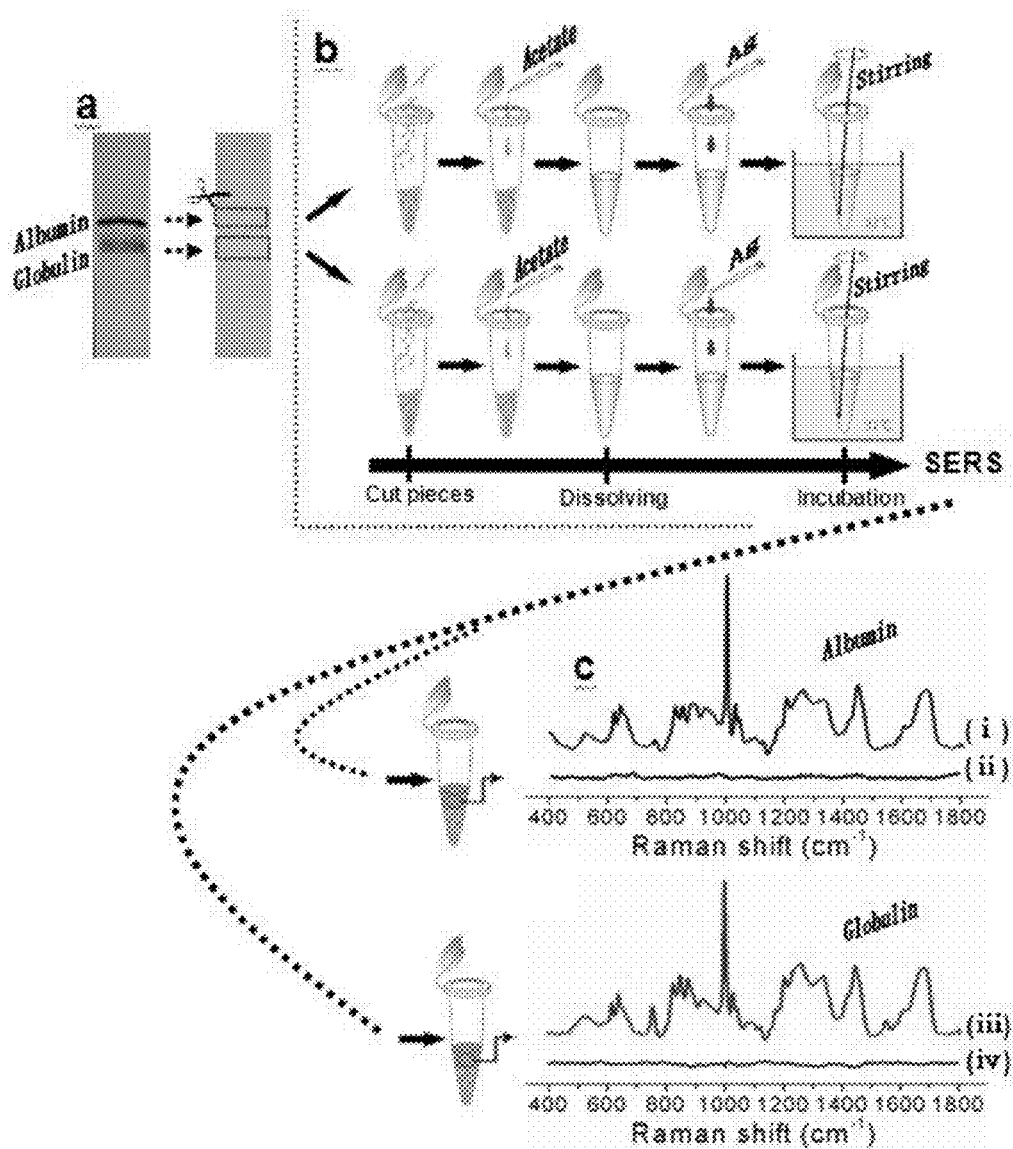
FIG. 1 is a schematic diagram illustrating preparation and SERS detection of mixed body fluid-SERS enhancing substrates solution: (a) Shows stained band of serum protein (left) and unstained band (right) resulted from separation via cellulose acetate electrophoresis; (b) indicates preparation of mixed protein-silver nanoparticles solution; (c) displays SERS of serum protein. X axis represents Raman shift measured in wavenumber.
Figure 2:
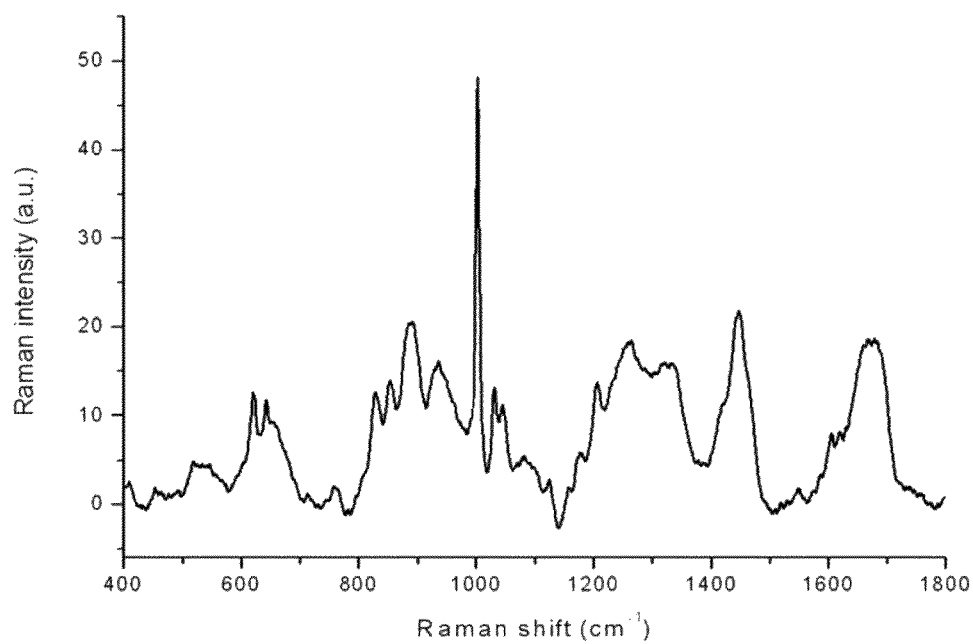
FIG. 2 indicates SERS of mixed solution of blood and silver SERS enhancing substrates. X axis represents Raman shift measured in wavenumber, and y axis represents relative intensity of Raman spectrum with arbitrary units.
Figure 3:
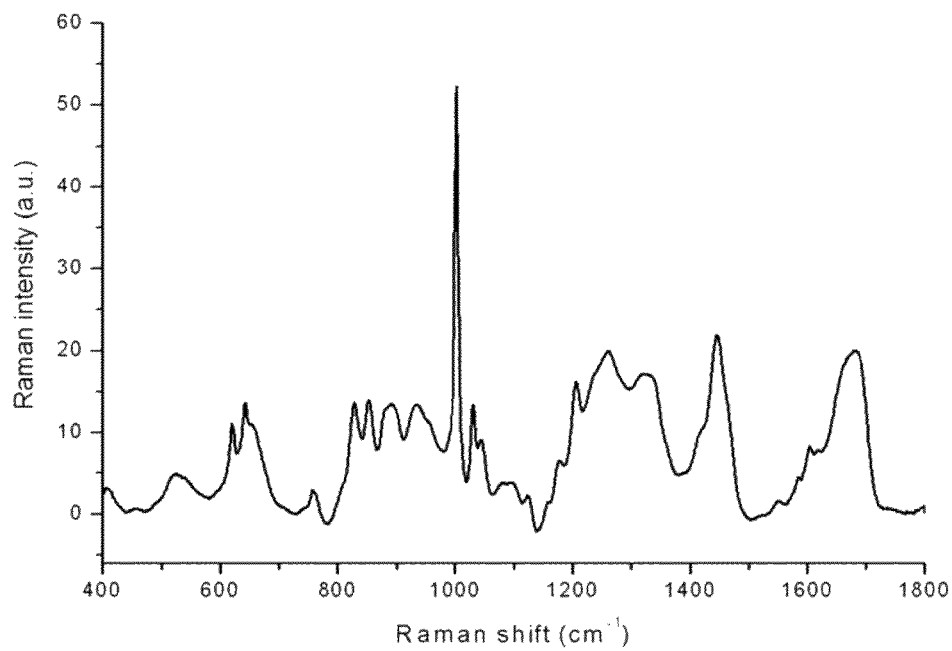
FIG. 3 is a comparison diagram with FIG. 1. X axis represents Raman shift measured in wavenumber, and y axis represents relative intensity of Raman spectrum with arbitrary unit.
Figure 5:
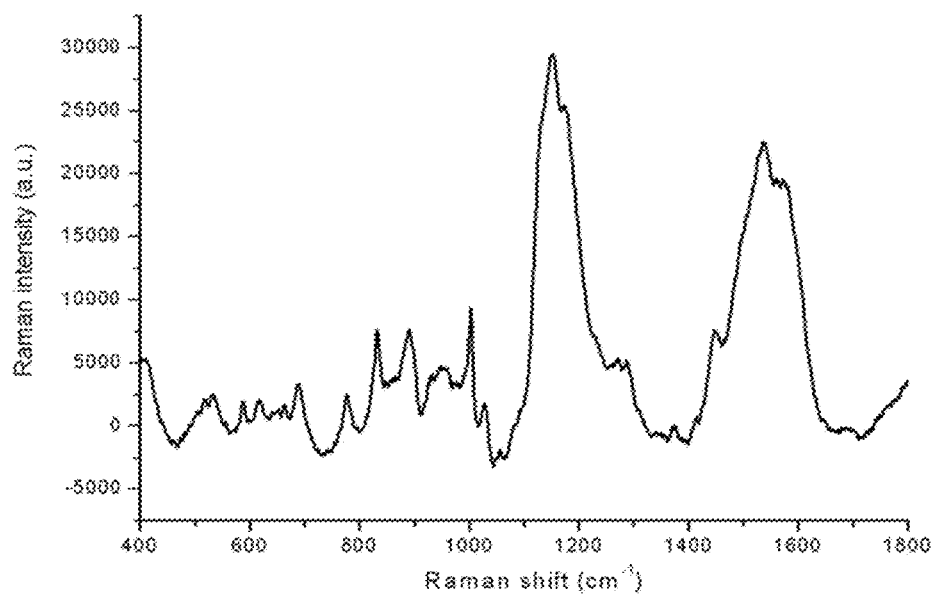
FIG. 5 shows SERS of mixed solution of blood and gold SERS enhancing substrates. X axis represents Raman shift measured in wavenumber, and y axis represents relative intensity of Raman spectrum with arbitrary units.

Wavelength of the light used in FIGS. 2, 3 and 5 is 785 nm, with the power of 0.1-20 mW. Y axis represents intensity of spectrum line, and x axis stands for location of every characteristic line marked with wavenumber ($cm^{-1}$).

EXEMPLIFICATION

Example 1

Preparation of Mixed Blood-Silver Sol Solution and SERS Detection

1) Preparation of silver sol: silver sol is prepared by reduction with hydroxylamine hydrochloride. 12 ml of sodium hydroxide (0.1 mol) solution was added to 10 ml of hydroxylamine hydrochloride (0.06 mol) solution. The hydroxylamine/sodium hydroxide solution was then added rapidly to 180 ml of silver nitrate (0.0011 mol) solution under vigorous stirring. Then a grey-brown colloidal solution resulted, followed by rotating with centrifuge at 4500 rpm for 12 min. Then discard the upper clear layer resulted from centrifugation and seal the bottom condensed layer of silver sol in the dark at room temperature for use.

2) Cellulose acetate electrophoresis: divide different blood samples into group A and B, which simultaneously operated as follows: the two groups of blood samples are centrifuged at 800 rpm for 12 min. Then extract upper serum layer resulted as samples for use below. Spot on two strips of cellulose acetate membranes with sample applicator. After that, stick the two strips on filter paper on both sides of the holder of electrophoresis chamber, followed by electrophoresis with voltage of 180 V for 45 min. When electrophoresis is over, remove both strips, one of which is taken to rinse for 12 min then dried on filter paper. The other strip is stained with amido black 10 B for 3 min, then rinsed until blue background fades entirely and dried on filter paper. After staining, five bands appear on the membrane strip. From anode to cathode, they are albumin, α1 globulin, α2 globulin, β globulin and γ globulin, respectively. For comparison with the stained strip, the first protein spectral band close to anode, i.e., albumin, on the membrane strip directly rinsed is cut and collected in a 1.5 ml test tube.

3) The preparation of mixed serum protein-silver nanoparticles solution: add 200 μl of glacial acetic acid to the test tube containing spectral band of serum protein. Keep stirring at room temperature until the membrane strip fully dissolved, appearing a limpid colloidal solution. Under water bath at 37° C., add 450 μl of silver sol prepared in advance to the test tube with adequately stirring until membrane strips precipitate as floccule. Stop stirring and keep it in a water bath at 37° C. for 45 min. Remove the upper aqueous phase resulted which is the mixed solution of serum protein and silver nanoparticles with pipette to a aluminum object plate, drying naturally.

4) SERS detection: obtain SERS spectrum of albumin respectively by detecting the samples derived from the groups of A and B with confocal Raman spectrometer. The samples are irradiated by the light (λ=785 nm) in the detection, with power of 3.75 mW and collection range of 400-1800 $cm^{-1}$. SERS spectrum of albumin for group A and B are shown in FIGS. 2 and 3 respectively. Notably, SERS spectrum for group B is obtained using the same method as group A.

Figure 4:
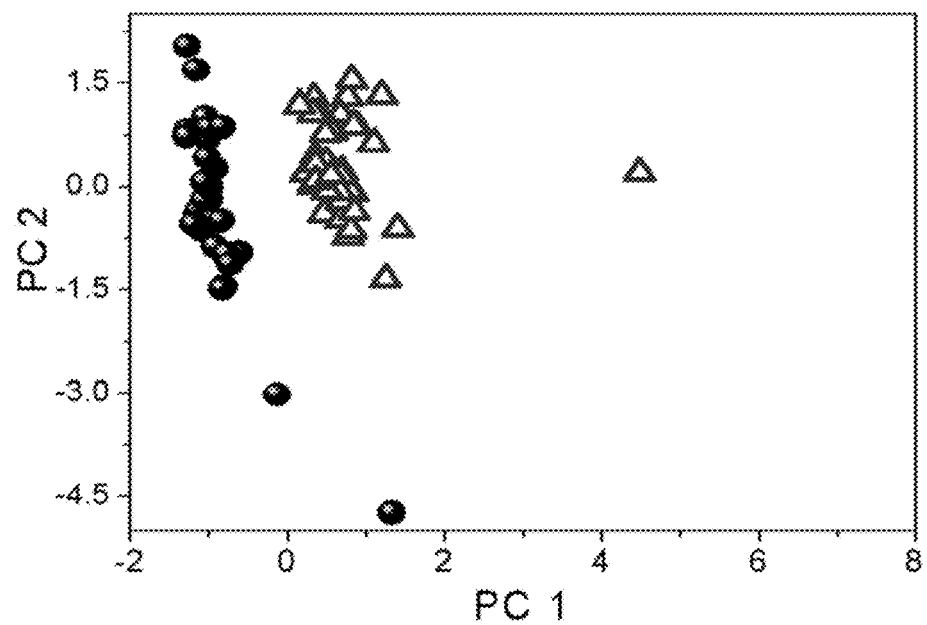
FIG. 4 is scatterplots obtained through PCA analysis of two kinds of blood samples mentioned. X axis and y axis represent the first and second principal component with arbitrary unit respectively. Black dots and red triangles represent SERS spectrum of plasma from group A and B respectively.

5) SERS data of albumin from group A and B are analysed by SPSS software, with which data are transposed to generate sample matrix. PCA is applied to calculate variance of spectral data and build the qualitative predictive model based on the standards. Specific steps are listed as follows: a) calculate covariance matrix of the samples; b) calculate covariance matrix eigenvector of the samples and sort them descendingly; c) define principal component according to the eigenvalue, and calculate contribution rate of each principal component; d) select principal component with rate of cumulative contribution higher than 70% based on contribution rate. FIG. 4 shows the scatterplots generated by the principal component chosen.

Example 2

Preparation of Mixed Blood-Gold Sol Solution and SERS Detection

1) Preparation of gold sol: chloroauric acid (10 mg) is dissolved in 100 ml of deionized water and brought to boiling heated at 100° C. A solution of 2% sodium citrate (2 ml) is dropped with vigorous stirring. The solution is kept on boiling for fifteen minutes. Let the gold sol resulted cool naturally, followed by rotating with centrifuge. Discard the upper clear layer and seal the bottom condensed gold sol layer in the dark at room temperature for use.

2) Cellulose acetate electrophoresis: divide blood samples into group A and B. Simultaneous doing is operated as follows: rotate blood samples with centrifuge at 1000 rpm for 10 min. Then extract upper serum layer resulted as samples for use. Spot on two strips of cellulose acetate membranes with sample applicator. After that, stick the two strips on both sides of filter paper on the chamber holder, followed by electrophoresis with voltage of 15 V/cm for 55 min. When electrophoresis is over, remove both strips, one of which is taken to rinse for 10 min then dried on filter paper. The other strip is stained with amido black 10 B for 2 min, then rinsed until background blue fades entirely and dried on filter paper. After staining, five bands appear on the strip. From anode to cathode, they are albumin, α1 globulin, α2 globulin, β globulin and γ globulin, respectively. For comparison with the stained strip, the first protein spectral band close to the anode, i.e., albumin, on the strip directly rinsed is cut and collected in a 1.5 ml test tube.

3) Preparation of mixed serum protein-gold nanoparticles solution: add 150 μl of glacial acetic acid to the test tube containing spectral band of serum protein. Keep stirring at room temperature until the membrane strip fully dissolved, appearing a limpid colloidal solution. Under water bath at 50° C., add 200 μl of gold sol prepared in advance to the test tube with adequately stirring until membrane strips precipitate as floccule. Stop stirring and keep it in a water bath at 50° C. for 28 min. Remove the upper aqueous layer resulted which is the mixed serum protein-gold nanoparticles solution with pipette to a aluminum object plate, drying naturally.

4) SERS detection: confocal Raman spectrometer is used in the study of SERS spectrum of albumin. The samples are irradiated by the light (λ=785 nm) in the detection, with power of 0.1 mW and collection range of 450-1750 $cm^{-1}$ SERS spectrum of albumin for group A is shown in FIG. 5. Notably, SERS spectrum for group B is obtained using the same method as group A.

The process of PCA analysis is the same as that in example 1.

Example 3

SERS Detection of Urine

1) Preparation of silver sol: silver sol is prepared by aqueous reduction of silver nitrate with sodium citrate. 10 mg of silver nitrate was dissolved in 50 ml of deionized water and brought to boiling at 100° C. A solution of 2% sodium citrate (1 ml) is dropped with vigorous stirring. The solution is kept on boiling for six hours. Let the gold sol resulted cool naturally, followed by rotation with centrifuge. Discard the upper clear layer and seal the bottom layer of condensed colloid silver in the (lark at room temperature for use.

Figure 6:
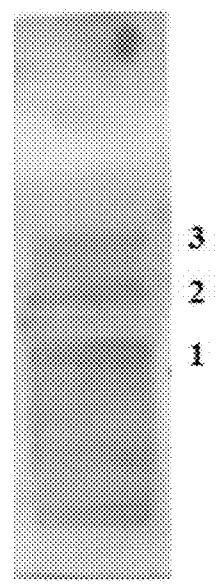
FIG. 6 displays silver staining diagram of urine treated via cellulose acetate electrophoresis.

2) Cellulose acetate electrophoresis: divide urine samples into group A and B. Simultaneous doing is operated as follows: urine sample was spotted on two strips of cellulose acetate membranes with sample applicator. After that, stick two strips on both sides of filter paper on the chamber holder, followed by electrophoresis with voltage of 21 V/cm for 40 min. When electrophoresis is over, remove both strips, one of which is taken to be stained with silver staining solution for 4 min, then rinsed in distilled water until background fades entirely and dried on filter paper. After staining, three protein bands appeared on the strip as shown in FIG. 6, which is cut and collected in a 1.5 ml test tube.

3) Preparation of mixed solution of serum protein and silver nanoparticles: add 180 μl of glacial acetic acid to the test tube containing protein bands. Keep stirring at room temperature until membrane strips fully dissolved, appearing a limpid colloidal solution. Under water bath at 42° C., add 220 p. 1 of silver sol prepared in advance to the test tube with adequately stirring until membrane strips precipitate as floccule. Stop stirring and keep it in a water bath at 42° C. for 30 min. Remove the upper aqueous layer resulted which is the mixed solution of urine protein and silver nanoparticles with pipette to a aluminum object plate, drying naturally.

Figure 7:
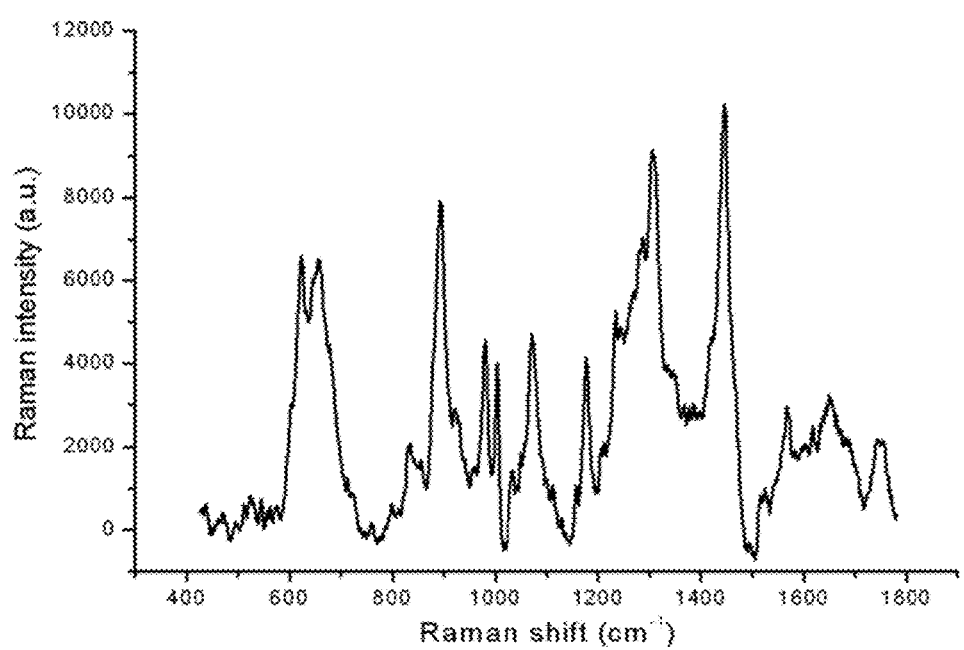
FIG. 7 indicates SERS of mixed solution of urine and silver SERS enhancing substrates. X axis represents Raman shift measured in wavenumber, and y axis represents relative intensity of Raman spectrum with arbitrary units.

4) SERS detection: confocal Raman Spectrometer is used in the study of SERS spectrum of urine protein. The samples are irradiated by the light ($\lambda$=785 nm) in the detection, with power of 0.13 mW and collection range of 425-1780 cm$^{-1}$. SERS spectrum of urine protein for group A is shown in FIG. 7. Notably, SERS spectrum for group B is obtained using the same method as mentioned in the above except urine samples for contrast is used.

The process of PCA analysis is the same as that in example 1.

Example 4

SERS Detection for Serum Protein of Healthy People and Gastric Cancer Patients

1) Preparation of silver sol: silver sol was prepared by aqueous reduction of silver nitrate with sodium citrate. 15 mg of silver nitrate was dissolved in 75 ml of deionized water and brought to boiling at 100° C. A solution of 2% sodium citrate (1.5 ml) is dropped with vigorous stirring. The solution is kept on boiling for five hours. Let the gold sol resulted cool naturally, followed by rotation with centrifuge. Discard the upper clear layer and seal the bottom condensed colloid silver layer in the dark at room temperature for use.

6) Cellulose acetate electrophoresis: rotate the blood sample of gastric cancer patients identified via hospitals at 1000 rpm for 10 min. Take upper serum layer as samples, which were spotted on two strips of cellulose acetate membranes with sample applicator. After that, stick two strips on both sides of filter paper on the chamber holder, followed by electrophoresis with voltage of 15 V/cm for 55 min. When electrophoresis is over, remove both strips, one of which is taken to rinse for 10 min and dried on filter paper. The other strip is stained with amido black 10 B for 2 min, then rinsed until background blue fades completely and taken out for drying on filter paper. After staining, five bands appear on the membrane strip. From anode to cathode, they are albumin, $\alpha 1$ globulin, $\alpha 2$ globulin, $\beta$ globulin and $\gamma$ globulin, respectively. For comparison with the stained strip, band containing five protein mentioned above which are directly rinsed on the strip is cut and collected in a 1.5 ml test tube.

3) Preparation of mixed solution of serum globulin and silver nanoparticles: add 150 μl of glacial acetic acid to the test tube containing serum globulin bands. Keep stirring at room temperature until the membrane strips fully dissolved, appearing a limpid colloidal solution. Under water bath at 37° C., add 200 μl of silver sol prepared in advance to the test tube with adequately stirring until membrane strips precipitate as floccule. Stop stirring and keep it in a water bath at 37° C. for 32 min. Remove the upper aqueous layer resulted which is the mixed solution of serum globulin and silver nanoparticles with pipette to a aluminum object plate, drying naturally.

4) SERS detection: confocal Raman spectrometer is used in the study of SERS spectrum of serum globulin. The samples are irradiated by the light ($\lambda$=785 nm) in the detection, with power of 0.1 mW and collection range of 442-1772 cm$^{-1}$.

Figure 8:
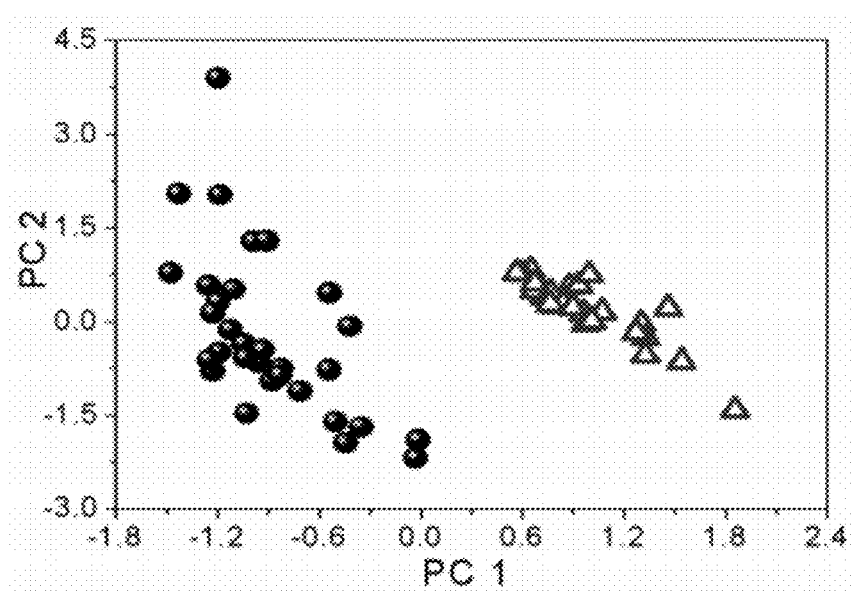
FIG. 8 is a clustering scheme derived from PCA of body fluid belonging to healthy people and gastric cancer patients. X axis and y axis represent the first and second principal component with arbitrary unit respectively. Black dots and red triangles stand for plasma of healthy people and gastric cancer patients respectively.

5) discriminant analysis: based on PCA method mentioned in example 1, build analytical model of SERS spectrum involving healthy people and gastric cancer patients. Then Scores corresponding to each of principal component is calculated using PCA. With x axis and y axis representing the first and second principal component, scatterplots relevant to blood samples of healthy people and gastric cancer patients is made as shown in FIG. 8, where dots (PC1<0.3) and triangles (PC1>0.3) represent blood of healthy people and gastric cancer patients respectively Blood can be differentiated when PC1 value of gastric patient's blood is greater than 0.3.

What is claimed is:

1. A body fluid detection method using surface enhanced Raman spectroscopy SERS comprising:
   a) treating body fluid sample into aqueous phase in an upper layer and solid phase in a bottom layer;
   b) dividing the upper aqueous phase equally into two parts and electrophoresing appropriate amount of each part simultaneously by membrane electrophoresis;
   c) staining one of the parts to compare with the other unstained part's position in membrane electrophoresis substrates;
   d) cutting off the unstained samples together with the said substrates at the same position when fixing the unstained part's position in the membrane electrophoresis substrates;
   e) bringing the unstained part to contacting with a proper glacial acetic acid at room temperature and mixing them to form limpid colloid, then adding enhancing substrates for Raman spectroscopy, mixing them up and keeping incubating and stirring at 25-65 Celsius; stopping stirring but continuing to incubate for 10-40 min when solid impurities precipitating, then taking said mixture of body fluid samples and said enhancing substrates for Raman spectroscopy which is the upper layer formed while standing to be tested through surface enhanced Raman spectroscopy:
   f) setting up SERS database by repetition involving different body fluid samples following the same procedures as described above;
   g) carrying out cluster analysis of SERS database using Principal Component Analysis PCA method and building a SERS analytical model to obtain a scatterplot corresponding to different body fluid samples.

2. The body fluid detection method according to claim 1, wherein respective SERS of normal people and patients' body fluid is obtained following the procedures from a) to e)

as described in claim 1 in order to build SERS database; the PCA method is applied in the cluster analysis of the database to build SERS analytical model, then the scatterplot is made, with which body fluid can be further distinguished by identification of SERS of normal people and patients.

3. The body fluid detection method of claim 1, wherein the body fluid includes blood, serum, lymph, cerebrospinal fluid, urine, saliva, lacrimal fluid, sweat, cell extracts, tissue homogenate, vaginal discharge or seminal fluid.

4. The body fluid detection method of claim 1, wherein the staining method is amido black 10 B staining, coomassie brilliant blue staining or silver staining method.

5. The body fluid detection method of claim 1, wherein the said enhancing substrates for Raman spectroscopy are silver sol or gold sol, the said mixture is mixed protein-silver sol or protein-gold sol solution.

6. The body fluid detection method of claim 1, wherein the said electrophoretic medium used in the membrane electrophoresis is cellulose acetate membrane, nitrocellulose membrane, nylon membrane or polyvinylidene fluoride membrane.

7. The body fluid detection method of claim 1, wherein the said surface enhanced Raman spectroscopy has a wavelength of the laser light in the range from 400 to 850 nm, and is selected spectral range of 400-4000 $cm^{-1}$.

8. The body fluid detection method using liquid surface enhanced Raman spectroscopy of claim 1 is used to apply in the diagnosis or screening of diseases.

\* \* \* \* \*